United States Patent [19]
Zhang et al.

[11] Patent Number: 5,948,944
[45] Date of Patent: Sep. 7, 1999

[54] TWO-STAGE DINITROTOLUENE PRODUCTION PROCESS

[75] Inventors: Chunjie Zhang, Lake Charles; Buford T. Pennington, Sulphur; Jeffrey W. Baird; Allen B. Quakenbush, both of Lake Charles, all of La.; Stephen L. Goldstein, Glen Mills, Pa.; Donald L. Lickei, Waterbury, Conn.; Peter J. Whitman, Glen Mills, Pa.

[73] Assignee: Arco Chemical Technology, L.P., Greenville, Del.

[21] Appl. No.: 09/197,622

[22] Filed: Nov. 18, 1998

[51] Int. Cl.$^6$ .......................... C07C 205/00; C06B 25/04; D03D 23/00
[52] U.S. Cl. ....................... 568/934; 568/932; 149/109.6; 149/105
[58] Field of Search .......................... 149/109.6; 568/934

[56] References Cited

U.S. PATENT DOCUMENTS

| | | |
|---|---|---|
| 2,362,743 | 11/1944 | Crater ....................................... 260/645 |
| 5,001,272 | 3/1991 | Mason ....................................... 568/934 |
| 5,057,632 | 10/1991 | Imm et al. ................................. 568/934 |
| 5,099,078 | 3/1992 | Quakenbush ............................. 568/934 |
| 5,099,080 | 3/1992 | Quakenbush ............................. 568/934 |
| 5,245,092 | 9/1993 | Quakenbush ............................. 568/934 |
| 5,302,763 | 4/1994 | Quakenbush ............................. 568/934 |
| 5,354,924 | 10/1994 | Mason ..................................... 568/934 |
| 5,488,187 | 1/1996 | Mason ..................................... 568/932 |

*Primary Examiner*—Charles T. Jordan
*Assistant Examiner*—Aileen J. Baker
*Attorney, Agent, or Firm*—Dale Lynn Carlson; Wiggin & Dana

[57] ABSTRACT

A multi-step process for producing DNT employing a mono-nitration step in a single liquid phase at an elevated temperature using a carefully controlled amount of water, followed by a phase separation step prior to dinitration of the MNT present in the resulting organic phase. This process results in a DNT product with a desired isomer ratio of 2,4-DNT to 2,6-DNT and provide relatively fast nitration rates with less by-products.

8 Claims, No Drawings

TWO-STAGE DINITROTOLUENE PRODUCTION PROCESS

FIELD OF THE INVENTION

This invention relates generally to the production of dinitrotoluene ("DNT"). More particularly, the invention relates to an improved process for producing DNT using a phase separation between the mononitration and dinitration steps.

BACKGROUND OF THE INVENTION

Dinitrotoluene (DNT) is a versatile and valuable chemical intermediate which is widely used in the production of toluene diisocyanate.

DNT is produced by a process involving the nitration of toluene first to mononitrotoluene and then to DNT. Historically, the nitration reaction has been carried out commercially using a mixed acid system, namely, nitric acid and sulfuric acid. However, as a result of recent developments in this field, an alternative, improved process is now available for the commercial production of DNT which, among other things, obviates the need for using sulfuric acid in the nitration of toluene. See for example U.S. Pat. No. 5,001,272, issued Mar. 24, 1991 to Mason, and U.S. Pat. No. 5,009,078, issued Mar. 24, 1992 to Quakenbush, U.S. Pat. No. 5,302,763, issued Apr. 12, 1994 to Quakenbush, U.S. Pat. No. 5,354,924, issued Oct. 11, 1994 to Mason, and U.S. Pat. No. 5,488,187, issued Jan. 30, 1996 to Mason. All of these patents are incorporated herein by reference in their entirety.

The nitration reaction, whether using a mixed acid system or nitric acid by itself, typically results in the generation of undesirable byproducts, as well as a weight ratio of 2,4-DNT to 2,6-DNT isomers that may be higher or lower than desired. Illustrative undesirable impurities that typically result from the production of DNT include phenolic impurities, such as cresol compounds.

There is a continuing need in the DNT manufacturing community for a process, that advantageously can be operated continuously, and that provides a relatively fast reaction rate, a relatively low amount of impurities, and a DNT product having a desirable 2,4-DNT to 2,6-DNT isomer ratio. The present invention provides one answer to that need.

SUMMARY OF THE INVENTION

In one aspect, the present invention relates to a process for producing dinitrotoluene comprising the steps of:

(a) reacting toluene with nitric acid in a single liquid phase reaction in a first reaction zone at an elevated temperature to provide a single phase mononitrotoluene-containing product mixture, using a reaction mixture that is free of sulfuric acid and that comprises a molar ratio of said nitric acid to said toluene of from 20:1 to 30:1, said reaction being conducted using a combination of fresh and recycled aqueous nitric acid, said combination having a nitric acid concentration not exceeding 75% based upon the weight of nitric acid plus water in said dilute aqueous nitric acid, (b) phase-separating said single phase mononitrotoluene-containing product mixture into two phases by cooling said mononitrotoluene-containing product mixture to a temperature below said elevated temperature in order to provide an organic phase comprising a major amount of said mononitrotoluene, and an aqueous phase comprising a major amount of said water, and recycling at least a portion of said aqueous phase into said first reaction zone in order to incorporate said recycled aqueous nitric acid into said reaction mixture, and (c) reacting, in a second reaction zone, said mononitrotoluene in said organic phase with concentrated nitric acid having an acid concentration of at least 90% by weight, at a second elevated temperature, using a molar ratio of nitric acid to mononitrotoluene of 10:1 to 20:1, in order to provide said dinitrotoluene in a dinitrotoluene-containing product mixture, wherein the amount of 2,4-dinitrotoluene in said dinitrotoluene-containing product mixture does not exceed 81% based upon the total amount of 2,6-dinitrotoluene plus said 2,4-dinitrotoluene in said dinitrotoluene-containing product mixture. Steps (a) and (b) are preferably closely associated to facilitate the transfer and recycling of a desired amount of water that is isolated by virtue of the phase-separation of step (b) back into step (a). Advantageously, this process is conducted in a continuous fashion, although the process can be carried out in batch or semi-continuous mode if desired.

This and other aspects will become apparent upon reading the following detailed description of the invention.

DETAILED DESCRIPTION OF THE INVENTION

It has now been surprisingly found, in accordance with the present invention, that the reaction rate and desired DNT product quality in terms of desired isomer ratio resulting from a single liquid phase nitration reaction to produce DNT is dramatically improved by employing a certain reaction protocol. More specifically, the present invention employs a phase separation step between the mononitration step to produce mononitrotoluene ("MNT"), and the dinitration step to produce the desired dinitrotoluene. The phase separation step provides an aqueous phase that is suitably recycled to the mononitration reaction zone to provide water replenishment and insure that the nitric acid in the mononitration reaction zone does not become undesirably concentrated. Without wishing to be bound by any particular theory, the present inventors have found that the amount of water present in the mononitration reaction zone plays a key role in determining the amount of 2,4-DNT later produced in the dinitration step, as well as a key role in determining the rate of the mononitration reaction step. Further, removal of the aqueous phase prior to the dinitration reaction serves to enhance the rate of the dinitration reaction, thus enabling the entire reaction sequence to be effected within an hour or less.

This result is particularly surprising in view of the earlier finding of the present inventors, namely that a "one-step" DNT production process (in the absence of sulfuric acid) typically does not provide DNT having a desired (i.e., about 80/20) molar ratio of 2,4-DNT to 2,6-DNT. Instead, the resulting product contains too much 2,4-DNT, necessitating further processing to provide DNT product having the desired amount of these isomers. Such further processing can be prohibitively expensive. In contrast, the present invention provides a straightforward method for providing the desired isomer ratio without the need for subsequent processing to achieve this result.

The process of the present invention is a multi-step process. The first step (i.e., step (a)) comprises a mononitration step that is effected at an elevated temperature, generally from 30 to 100 (and preferably from 40 to 60, more preferably from 35 to 55) degrees Centigrade. The amount of water present in the mononitration reaction mixture is suitably maintained within a range of from 67 weight percent to 74 weight percent, based upon the total amount of nitric acid plus water employed. Advantageously, the mononitration reaction is carried out in a loop reactor in view of the single-phase nature of this reaction.

The mononitration step is followed by a cooling step (i.e., step (b)) in order to cause phase separation of the product mixture from step (a), into aqueous and organic phases. Once separated, the aqueous phase, or, portion, therefore, is returned to the toluene reacting step. The third step (i.e., step (c)) comprises reacting the MNT in the organic phase with concentrated nitric acid at an elevated temperature of at least 30 degrees Centigrade, in order to provide a relatively fast reaction rate.

The process of the present invention is suitably carried out in two reaction zones (or more), including a mononitration reaction zone, and a dinitration reaction zone. At least a portion (and preferably essentially all) of the aqueous phase from the phase separation step is suitably recycled back into the mononitration reaction zone. This recycling insures that the nitric acid in mononitration reaction zone does not become overly concentrated. Indeed, the present inventors have found that the use of overly concentrated (i.e., over 90 weight percent acid) nitric acid in the mononitration reaction zone tends to cause a problem in the dinitration step. More specifically, the resulting DNT product is undesirably high in 2,4-DNT isomer content, relative to the amount of 2,6-DNT isomer produced.

The recycle of the aqueous phase into the mononitration zone is an important aspect of the present invention for at least one key reason, because a large amount of water carried over to the dinitration step dilutes the concentrated nitric acid feed in the dinitration step and therefore, terminates the dinitration reaction. Using this methodology, the aqueous phase is easily and conveniently recycled directly into the mononitration reaction step without any need for an elaborate purification in the downstream process that requires multisteps and higher energy usage.

Cooling to effect the desired phase separation of step (b) is suitably accomplished by reducing temperature of the MNT product mixture by any suitable means of heat exchange.

The third step in the process of the present invention, namely dinitration, is suitably carried out at an elevated temperature that is generally in the range of from 30 to 100 (preferably from 45 to 80) degrees Centigrade. The dinitration can be accomplished in a plug flow reactor (PFR) or a continuous stirred tank reactor (CSTR), although a CSTR loop reactor is particularly advantageous. The dinitration may be effected in a single stage, or it may be conducted in multiple stages, advantageously in series. The use of multiple stages, e.g., a "split" reactor with several stages in series, facilitates enhancing the efficiency of heat transfer attributable to the exotherm associated with the dinitration reaction, so that the temperature during the dinitration reaction is as desired for the reactor utilized. The concentrated nitric acid used as a reactant for the dinitration step is preferably at least 90%, more preferably at least 95%, by weight of acid based upon the total amount of acid plus water employed.

The molar ratio of nitric acid to toluene use in step (a) is suitably from 20:1 to 30:1, and for step (c) is from 10:1 to 20:1. Operating within this range of molar ratios maximizes the production of the desired product and minimizes by-product formation due to relatively fast reaction rates for both mononitration and dinitration steps.

After forming the desired DNT product, a "phase separating agent", such as an alkaline metal or alkaline earth metal, is suitably employed to separate unreacted nitric acid from the DNT product, as disclosed in U.S. Pat. No. 5,001,272, incorporated herein by reference in its entirety. The phase separating agent, if used, is suitably employed in an amount of from 0.5 to 1.5 percent, per one percent by weight of nitric acid in the product mixture. This phase separation using a phase separating agent is suitably carried out in by distillation in a distillation column.

Washing with water and a basic solution produces a purified DNT product. These wash waters are free of phenolic impurities, such as the nitrocresol impurities typically found in wastewater produced using mixed (sulfuric/nitric) acid processes.

The following examples are intended to illustrate, but in no way limit the scope of, the present invention. All parts and percentages are by weight unless otherwise specified.

EXAMPLE 1

Multi-Stage DNT Production

Toluene, concentrated nitric acid, and an aqueous phase passing from a phase separator after a mononitration reaction, were fed into a loop reactor. The molar ratio of nitric acid feed including concentrated nitric acid and the nitric acid from the recycled aqueous phase was 28:1 and the concentration of the nitric acid feed was 71%. Mononitration was carried out in a single liquid phase at a reaction temperature of 45 degrees Centigrade in a reaction time of one minute. The product was cooled to cause phase separation, thus providing an aqueous phase and an organic phase. The aqueous phase was recycled back to the mononitration reaction zone in order to maintain a 70% nitric acid concentration in that zone.

The organic phase was dinitrated, in a second reaction zone in the form of a CSTR loop reactor, at a reaction temperature of 45 degrees Centigrade, using 94% nitric acid (in water) in a molar ratio of nitric acid to MNT of 15:1. The resulting DNT product mixture had a 2,4-DNT content of from 80.3% to 80.5% by weight, based upon the total amount of 2,4-DNT plus 2,6-DNT in the product mixture. One hundred percent conversion of the MNT to DNT was achieved in a reaction time of four minutes.

As a comparison, toluene was dinitrated in a single reaction zone in the form of a loop reactor using nitric acid having a 94% concentration and a molar ratio of nitric acid to toluene of 18 to 1. The resulting DNT product had a 2,4-DNT isomer amount of 81.5%, based upon the total amount of 2,4-DNT plus 2,6-DNT in the product mixture. This is considered to be an unacceptably high amount of 2,4-DNT isomer.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A process for producing dinitrotoluene comprising the steps of:

(a) reacting toluene with nitric acid in a single liquid phase reaction in a first reaction zone at an elevated temperature to provide a single phase mononitrotoluene-containing product mixture, using a reaction mixture that is free of sulfuric acid and that comprises a molar ratio of said nitric acid to said toluene of from 20:1 to 30:1, said reaction being conducted using a combination of fresh and recycled aqueous nitric acid, said combination having a nitric acid concentration not exceeding 75% based upon the weight of nitric acid plus water in said dilute aqueous nitric acid, (b) phase-separating said single phase mononitrotoluene-containing product mixture into two phases by cooling said mononitrotoluene-containing product mixture to a temperature below said elevated temperature in order to provide an organic phase comprising a major amount of said mononitrotoluene, and an aqueous phase comprising a major amount of said water, and recycling at least a portion of said aqueous phase into said first reaction zone in order to incorporate said recycled aqueous nitric acid into said reaction mixture, and (c) reacting, in a second reaction zone, said mononitrotoluene in said organic phase with concentrated nitric acid having an acid concentration of at least 90% by weight, at a second elevated temperature, using a molar ratio of nitric acid to mononitrotoluene of 10:1 to 20:1, in order to provide said dinitrotoluene in a dinitrotoluene-containing product mixture, wherein the amount of 2,4-dinitrotoluene in said dinitrotoluene-containing product mixture does not exceed 81% based upon the total amount of 2,6-dinitrotoluene plus said 2,4-dinitrotoluene in said dinitrotoluene-containing product mixture.

2. The process of claim 1 wherein said nitric acid employed in step (a) is present in said reaction mixture in a concentration of from 65% to 75 percent by weight, based upon the total amount of nitric acid plus water in said reaction mixture.

3. The process of claim 1 wherein the amount of said nitric acid present in said first reaction zone is from 67 to 74 percent by weight based upon the total amount of nitric acid plus water in said first reaction zone.

4. The process of claim 1 wherein the elevated temperature and the second elevated temperature are independently selected within a range of from about 35 to about 60 degrees Centigrade.

5. The process of claim 1 which comprises the additional step of diluting the organic phase from step (b) with added water before step (c) in order to reduce or minimize the risk of unwanted detonation of said organic phase.

6. The process of claim 1 wherein said cooling is effective in reducing the temperature of said mononitrotoluene-containing product mixture to a temperature not exceeding 30 degrees Centigrade.

7. The process of claim 1 wherein said first reaction zone comprises a loop reactor, and wherein said second reaction zone comprises a plug-flow or continuous stirred tank reactor.

8. The process of claim 1 which comprises the additional step of phase-separating unreacted nitric acid from dinitrotoluene in said dinitrotoluene-containing product mixture by contacting the dinitrotoluene-containing mixture with an alkaline metal or alkaline earth metal phase separating agent in an amount of from 0.5 to 1.5 percent by weight, based upon the weight of the product mixture.

* * * * *